ABSTRACT

United States Patent [19]

Weber

[11] 4,261,855
[45] Apr. 14, 1981

[54] NOVEL STILBENE COMPOUNDS

[75] Inventor: Kurt Weber, Basel, Switzerland

[73] Assignee: Ciba-Geigy Corporation, Ardsley, N.Y.

[21] Appl. No.: 44,608

[22] Filed: Jun. 1, 1979

Related U.S. Application Data

[63] Continuation of Ser. No. 894,469, Apr. 10, 1978, abandoned.

[30] Foreign Application Priority Data

Apr. 19, 1977 [LU] Luxembourg .............................. 77159

[51] Int. Cl.$^3$ ........................................... C07D 413/10
[52] U.S. Cl. .............................. 252/301.24; 427/158; 542/462
[58] Field of Search ................ 542/462; 252/301-324

[56] References Cited

U.S. PATENT DOCUMENTS

| | | | |
|---|---|---|---|
| 3,453,268 | 7/1969 | Dorlars et al. ........................ | 542/462 |
| 3,459,744 | 8/1969 | Dorlars et al. ........................ | 542/462 |
| 3,761,470 | 9/1973 | Strobel et al. ........................ | 542/462 |
| 3,789,012 | 1/1974 | Tuite .................................... | 252/301.24 |
| 3,830,848 | 8/1974 | Siegrist ............................... | 252/301.24 |
| 4,032,558 | 6/1977 | Fleck et al. .......................... | 252/301.24 |
| 4,039,531 | 8/1977 | Günther et al. ..................... | 252/301.24 |
| 4,061,860 | 12/1977 | Kormany et al. ................... | 252/301.24 |

FOREIGN PATENT DOCUMENTS 2712409  10/1977  Fed. Rep. of Germany .

Primary Examiner—Arthur P. Demers
Attorney, Agent, or Firm—Edward McC. Roberts

[57] ABSTRACT

Stilbene compounds of the formula

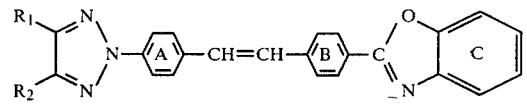

in which the rings A, B and C can carry non-chromophoric substituents, $R_1$ is hydrogen, alkyl which is unsubstituted or substituted by non-chromophoric substituents, or aryl which is unsubstituted or substituted by non-chromophoric substituents, and $R_2$ is a carboxyl group or a functional derivative thereof, a cyano group, a sulphonic acid ester group, a sulphonamide group or a sulphonyl group, and the use thereof as fluorescent brightening agents for high-molecular organic material.

13 Claims, No Drawings

NOVEL STILBENE COMPOUNDS

This is a continuation of application Ser. No. 894,469, filed on Apr. 10, 1978, now abandoned.

The present invention relates to novel 4-(2H-1,2,3-triazol-2-yl)-4-(benzoxazol-2-yl)-stilbene compounds, processes for their preparation and their use as optical fluorescent brightening agents for high-molecular organic material.

4-(1,2,3-Triazol-2-yl)-4′-(benzoxazol-2-yl)-stilbenes are known from German Offenlegungsschrift No. 2,535,613. It has now been found, surprisingly, that 4-(1,2,3-triazol-2-yl)-4′-(benzoxazol-2-yl)-stilbene compounds which have specific substituents on the triazole ring have particularly advantageous fluorescent brightener properties and that they are considerably more easily accessible than the triazolylstilbenes known hitherto.

The compounds according to the invention are of the formula

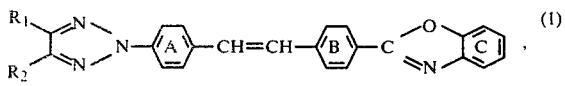 (1)

in which the rings A, B, and C can carry non-chromophoric substituents, $R_1$ is hydrogen, alkyl which is unsubstituted or substituted by non-chromophoric substituents, or aryl which is unsubstituted or substituted by non-chromophoric substituents, and $R_2$ is a carboxy group or a functional derivative thereof, a cyano group, a sulphonic acid ester group, a sulphonamide group or a sulphonyl group.

Examples of non-chromophoric substituents are: halogen atoms; alkyl groups, which can also be substituted, for example by halogen, cyano, hydroxyl, alkoxy, phenoxy, carboxylic acid groups and functional derivatives thereof or aryl radicals, preferably phenyl radicals; cycloalkyl groups; alkenyl groups; alkoxy groups, which can also be substituted, for example by halogen, hydroxyl, alkoxy, aryl groups, preferably phenyl, phenoxy or cyano; alkenyloxy groups; carboxylic acid groups or sulphonic acid groups and functional derivatives thereof; sulphonyl groups, for example alkyl- or phenylsulphonyl groups; or aryl or aryloxy groups, preferably phenyl or phenoxy groups, which can be substituted by one or more of the abovementioned radicals. Two adjacent radicals in the ring C can together also form the complement to an aromatic or non-aromatic carbocyclic or heterocyclic ring system, which can also be substituted, preferably to a nonaromatic carbocyclic ring.

Functional derivatives of sulphonic acid groups and carboxylic acid groups are, in particular, salts, esters and amides. Preferred salts are the alkali metal salts, alkaline earth metal salts, ammonium salts and amine salts, especially the sodium salts, potassium salts and ammonium salts. The amides can be unsubstituted or monosubstituted or disubstituted, for example by alkyl groups, on the nitrogen atom.

Aryl is an aromatic carbocyclic or heterocyclic ring, which can contain one or more of the above substituents. An unsubstituted or substituted phenyl radical is preferred.

Halogen is to be understood as meaning chlorine, bromine and fluorine, preferably chlorine and bromine and especially chlorine.

Within the scope of the formula (1), compounds of interest are, in particular, those of the formula

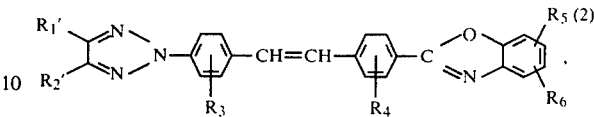 (2)

in which $R_1'$ is hydrogen, alkyl having 1 to 8 carbon atoms, alkyl having 1 to 4 carbon atoms which is substituted by halogen, cyano, alkoxy having 1 to 4 carbon atoms or phenyl, it being possible for the phenyl moiety of a phenylalkyl radical also to contain 1 or 2 substituents from the group comprising halogen and alkyl or alkoxy having 1 to 4 carbon atoms, or unsubstituted phenyl or phenyl substituted by 1 or 2 radicals from the group comprising halogen, cyano, alkyl or alkoxy each having 1 to 4 carbon atoms, carboxyl, carbalkoxy, sulphamoyl or alkylsulphonyl, $R_2'$ is cyano, a group of the formula —COOY, in which Y is hydrogen, an alkali metal ion, alkaline earth metal ion, ammonium ion or amine ion or an aliphatic, araliphatic or aromatic radical, a group of the formula —CON($Y_1$)($Y_2$) or —SO$_2$N($Y_1$)($Y_2$), in which $Y_1$ is hydrogen, an alkyl group having 1 to 8 carbon atoms, a hydroxyalkyl group having 2 to 4 carbon atoms or an unsubstituted phenyl radical or a phenyl radical substituted by chlorine or alkyl or alkoxy each having 1 to 4 carbon atoms and $Y_2$ is hydrogen, an alkyl group having 1 to 8 carbon atoms or a hydroxyalkyl group having 2 to 4 carbon atoms, or $Y_1$ and $Y_2$ together with the nitrogen atom to which they are bonded form a 5-membered to 7-membered non-aromatic heterocyclic ring, which can also contain 1 or 2 further hetero-atoms and can be substituted by alkyl groups having 1 to 4 carbon atoms; or alkylsulphonyl having 1 to 8 carbon atoms or a group of the formula —SO$_2$—O—Ar or —SO$_2$—Ar, in which Ar is unsubstituted phenyl or phenyl substituted by 1 or 2 radicals from the group comprising halogen, cyano and alkyl or alkoxy each having 1 to 4 carbon atoms, $R_3$ and $R_4$ independently of one another are hydrogen, chlorine or cyano, $R_5$ is hydrogen, chlorine, cyano or alkyl having 1 to 8 carbon atoms, or together with $R_6$ in the ortho-position is the complement to an alicyclic 5-membered or 6-membered ring, and $R_6$ is hydrogen, chlorine, cyano, alkyl having 1 to 8 carbon atoms, which is unsubstituted or substituted by cyano, carboxyl, carbalkoxy or chlorine, alkoxyalkyl having a total of 2 to 8 carbon atoms, alkoxy having 1 to 8 carbon atoms which is unsubstituted or substituted by cyano, or alkoxyalkoxy having a total of 2 to 8 carbon atoms, alkylsulphonyl having 1 to 8 carbon atoms, a group of the formula —CON($Y_1$)($Y_2$) or —SO$_2$N($Y_1$)($Y_2$), in which $Y_1$ is hydrogen, an alkyl group having 1 to 8 carbon atoms, a hydroxyalkyl group having 2 to 4 carbon atoms or an unsubstituted phenyl radical or a phenyl radical substituted by chlorine or alkyl or alkoxy each having 1 to 4 carbon atoms, and $Y_2$ is hydrogen, an alkyl group having 1 to 8 carbon atoms or a hydroxyalkyl group having 2 to 4 carbon atoms, or $Y_1$ and $Y_2$ together with the nitrogen atom to which they are bonded form a 5-membered to 7-membered non-aromatic heterocyclic ring, which can also contain 1 or 2 further hetero-atoms and can be substituted by alkyl groups having 1 to 4 carbon atoms; or phenylsulphonyl, phenoxysulphonyl, phenyl, phenoxy or phenylalkyl having 1 to 4 carbon atoms in the alkyl moiety, it being possible for the phenyl radicals of the last-mentioned 5 substituents also to be substituted by one or two radicals from the group comprising chlorine and alkyl and alkoxy each having 1 to 4 carbon atoms, or cyclohexyl or a group of the formula COOY, in which Y is hydrogen, an alkali metal ion, alkaline earth metal ion, ammonium ion or amine ion or an aliphatic, araliphatic or aromatic radical, or $R_6$ together with $R_5$ in the ortho-position is the complement to an alicyclic 5-membered or 6-membered ring.

An "aliphatic radical" is preferably alkyl having 1 to 8 carbon atoms or alkyl which is substituted by cyano, hydroxyl, halogen or alkoxy and has 1 to 6 carbon atoms in the alkyl moiety. An "araliphatic radical" is preferably a phenylalkyl radical, in which the alkyl radical has one to 4 carbon atoms and the phenyl nucleus can be substituted by 1 or 2 substituents from the group comprising alkyl, alkoxy or halogen. An "aromatic radical" is preferably phenyl, which is unsubstituted or monosubstituted or disubstituted by alkyl, alkoxy, halogen, cyano, carboxyl or carbalkoxy.

Preferred 5-membered to 7-membered non-aromatic heterocyclic rings are the piperidine, piperazine, morpholine, pyrrolidine, imidazoline and oxazolidine ring.

Preferred compounds are those of the formula

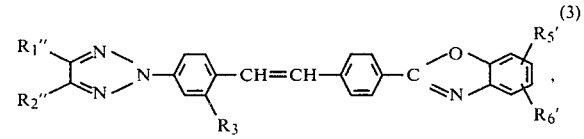

in which $R_1''$ is hydrogen, alkyl having 1 to 4 carbon atoms, benzyl or phenyl, $R_2''$ is cyano, a group of the formula COOY', in which Y' is hydrogen, an alkali metal ion, ammonium ion or amine ion or an alkyl group having 1 to 4 carbon atoms, or a group of the formula —CON($Y_1'$)($Y_2'$), in which $Y_1'$ and $Y_2'$ independently of one another are hydrogen or alkyl having 1 to 4 carbon atoms, or $Y_1'$ and $Y_2'$ together with the nitrogen atom to which they are bonded form a piperidine, dimethylmorpholine or morpholine ring, $R_3$ is hydrogen, chlorine or cyano, $R_5'$ is hydrogen, chlorine or alkyl having 1 to 4 carbon atoms, or together with $R_6'$ in the ortho-position is the trimethylene radical or tetramethylene radical, and $R_6'$ is hydrogen, chlorine, alkyl having 1 to 4 carbon atoms, alkoxy having 1 to 4 carbon atoms, alkylsulphonyl having 1 to 4 carbon atoms, a group of the formula $SO_2N(Y_1')(Y_2')$, in which $Y_1'$ and $Y_2'$ independently of one another are hydrogen or alkyl having 1 to 4 carbon atoms, or $Y_1'$ and $Y_2'$ together with the nitrogen atom to which they are bonded form a piperidine, dimethylmorpholine or morpholine ring; or phenylsulphonyl, phenoxysulphonyl, phenyl, phenoxy, phenylalkyl having 1 to 4 carbon atoms in the alkyl moiety, cyclohexyl, or a group of the formula COOY', in which Y' is hydrogen, an alkali metal ion, ammonium ion or amine ion or an alkyl group having 1 to 4 carbon atoms; or $R_6'$ together with $R_5'$ in the ortho-position is a trimethylene radical or tetramethylene radical.

Compounds of particular practical interest are those of the formula

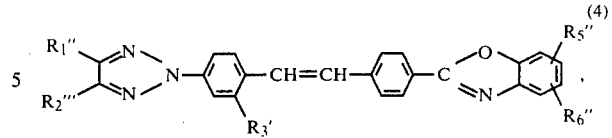

in which $R_1''$ is hydrogen, alkyl having 1 to 4 carbon atoms, benzyl or phenyl, $R_2'''$ is cyano, a carboxyl group or the sodium or potassium salt thereof, carbalkoxy having a total of 2 to 5 carbon atoms or a group of the formula —CON($Y_1''$)($Y_2''$), in which $Y_1''$ and $Y_2''$ independently of one another are hydrogen or alkyl having 1 to 4 carbon atoms, $R_3'$ is hydrogen or chlorine, $R_5''$ is hydrogen, chlorine or alkyl having 1 to 4 carbon atoms and $R_6''$ is hydrogen, alkyl having 1 to 4 carbon atoms, alkoxy having 1 to 4 carbon atoms, phenyl or phenoxy, and those of the formula

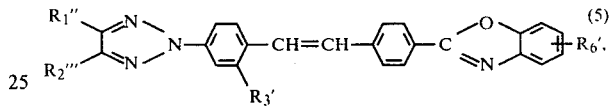

in which $R_1''$, $R_2'''$ and $R_3'$ are as defined in formula (4) and $R_6'$ is as defined in formula (3).

Amongst the compounds of the formula (4), preferred compounds are those in which $R_2'''$ is cyano or a carbalkoxy group.

Particularly preferred compounds are those of the formula

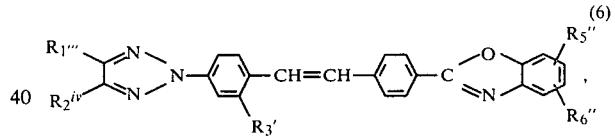

in which $R_1'''$ is hydrogen, methyl or phenyl and $R_2^{iv}$ is cyano, carbalkoxy having a total of 2 to 5 carbon atoms or a group of the formula —CON($Y_1''$)($Y_2''$), in which $Y_1''$ and $Y_2''$ independently of one another are hydrogen or alkyl having 1 to 4 carbon atoms, and $R_3'$, $R_5''$ and $R_6''$ are as defined in formula (4).

Compounds which have proved particularly valuable are those of the formula

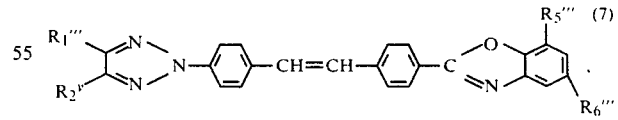

in which $R_1'''$ is hydrogen, methyl or phenyl, $R_2^v$ is carbalkoxy having a total of 2 to 5 carbon atoms, $R_5'''$ is hydrogen or methyl and $R_6'''$ is hydrogen, alkyl having 1 to 4 carbon atoms or methoxy, and especially those in which $R_1'''$ is hydrogen and $R_5'''$ and $R_6'''$ are hydrogen or methyl.

The compounds of the formula (1) can be prepared according to the invention by reacting a compound of the formula

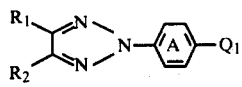

with a compound of the formula

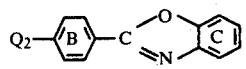

in which formulae $R_1$, $R_2$, A, B and C are as defined above and one of the two symbols $Q_1$ and $Q_2$ is a

group and the other is a group of the formula

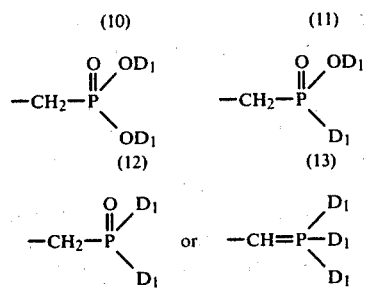

in which $D_1$ is an alkyl radical, which can be further substituted, or an aryl, cycloalkyl or aralkyl radical.

In $D_1$, alkyl radicals preferably have 1 to 4 carbon atoms, the preferred aryl radical is the phenyl radical, the preferred cycloalkyl radical is the cyclohexyl radical and the preferred aralkyl radical is the benzyl radical.

Preferably, one group $Q_1$ or $Q_2$ is a radical of the formula (10).

This process of preparation is advantageously carried out in inert solvents. Examples of such solvents are hydrocarbons, which can be chlorinated, such as toluene, xylene, chlorobenzene or dichlorobenzene, or alcohols, such as methanol, ethanol, isopropanol and butanol, glycols, glycol ethers, such as 2-methoxyethanol, hexanols, cyclohexanol and cyclooctanol, and also ethers, such as diisopropyl ether, tetrahydrofurane and dioxane, and also dimethylsulphoxide, formamide and N-methylpyrrolidone. Polar organic solvents, such as dimethylformamide and dimethylsulphoxide, are particularly suitable. Some of the reactions can also be carried out in water, with the addition of emulsifiers if necessary.

The temperature at which the reaction is carried out can vary within wide limits. It is determined: (α) by the stability of the solvent used towards the strongly basic alkali metal compounds, (β) by the reactivity of the reactants in the condensation reaction and (γ) by the effectiveness of the combination solvent/base as a condensing agent.

Accordingly, in practice the temperatures are generally between 0° and 100° C., especially when dimethylsulphoxide or dimethylformamide is used as the solvent. The preferred temperature range is from 10° to 60° C.

The reaction is preferably carried out in the presence of strongly basic alkali metal compounds. Strongly basic alkali metal compounds are, in particular, the hydroxides, amides and alcoholates of the alkali metals, those of lithium, sodium and potassium being of predominant interest. However, in principle and in particular cases, alkali metal sulphides and alkali metal carbonates, aryl-alkali metal compounds, for example phenyllithium, or strongly basic amines, for example trialkylammonium hydroxides, can be used successfully.

The preparation of compounds of the formula (4) by reacting a compound of the formula

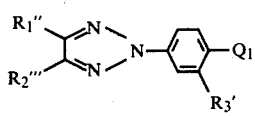

with a compound of the formula

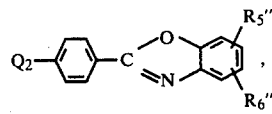

in which formulae $R_1''$, $R_2'''$, $R_3'$, $R_5''$ and $R_6''$ are as defined in formulae (4) and (5) and $Q_1$ and $Q_2$ are as defined in formulae (8) and (9), is preferred.

The starting compounds of the formulae (8), (9) and also (14) and (15) can be prepared by processes known per se.

Thus, the aldehydes of the formulae

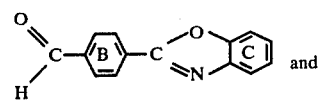

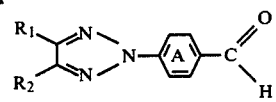

and also the corresponding aldehydes of the subsidiary formulae can be obtained, for example, by bromination (for example with the aid of N-bromosuccinimide) of the methyl compounds of the formulae

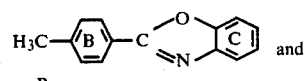

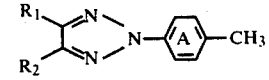

to the corresponding bromomethyl compounds and oxidation of these, for example with 2-nitropropane in a strongly alkaline medium, to the compounds of the formulae (16) and (17).

The phosphonate compounds, for example those of the formulae

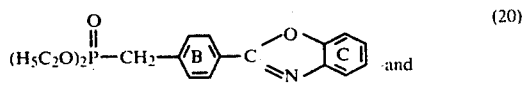

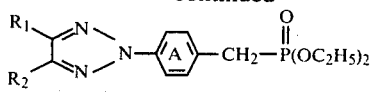

and also the corresponding phosphonates of the subsidiary formulae can be prepared, for example, by reacting the bromomethyl compounds, obtained from the compounds (18) and (19), with triethyl phosphite. The preparation of the novel starting materials and also the preparation of the compounds of the formula (19) by cyclisation is described in detail in the example section and is also a subject of the present invention. The starting materials used for the preparation of the end products according to the invention are preferably those which result in the compounds described initially as being particularly valuable. The preparation of the compounds of the formula (18) is carried out in accordance with known methods. The symbols $R_1$, $R_2$, A, B and C in the formulae (16) to (21) are as defined in formula (1).

The preparation of the compounds of the formulae (1) to (7) can also be carried out according to other methods known per se.

Thus, for example, compounds of the formula

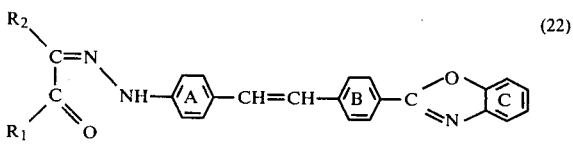

can be cyclised by the methods described in German Offenlegungsschrift No. 2,133,012 to compounds of the formula (1).

Compounds of the formula (22) can be obtained, for example, by diazotising an amino compound of the formula

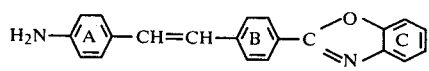

and coupling the resulting diazonium salt with a compound of the formula

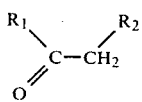

The compounds of the formulae (1) to (7) can also be prepared by, for example, reacting an o-aminophenol of the formula

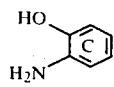

with a compound of the formula

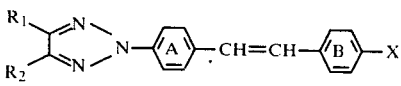

in which X is a carboxyl group or a functional derivative thereof, preferably an ester or a chloride, to give a compound of the formula (1), advantageously in an inert, high-boiling solvent.

In the formulae (22) to (26), the general symbols $R_1$, $R_2$, A, B and C are as defined in formula (1).

The compounds of the formulae (23) and (26) can be obtained from the corresponding 4-nitro-4'-carboxystilbenes and, respectively, 4-amino-4'-carboxystilbenes by building up the benzoxazole and, respectively, triazole ring in a manner known per se.

In the dissolved or finely divided state, the novel compounds defined above exhibit a more or less pronounced fluorescence. They can be used for optically brightening a wide variety of synthetic, regenerated man-made or natural organic materials, or substances which contain such organic materials.

Without any restriction being implied by the following classification, examples of organic materials which can be optically brightened are the following groups:

I. Synthetic organic materials of high molecular weight:

(a) Polymerisation products based on organic compounds containing at least one polymerisable carbon-carbon double bond, i.e. their homopolymers or copolymers as well as their aftertreatment products, for example crosslinking, grafting or degradation products, polymer blends or products obtained by modification of reactive groups, for example polymers based on $\alpha,\beta$-unsaturated carboxylic acids or derivatives of such carboxylic acids, especially on acrylic compounds (for example acrylates, acrylic acid, acrylonitrile, acrylamides and their derivatives or their methacrylic analogues), on olefin hydrocarbons (for example ethylene, propylene, styrenes or dienes, and also so-called ABS polymers), and polymers based on vinyl and vinylidene compounds (for example vinyl chloride, vinyl alcohol and vinylidene chloride), (b) Polymerisation products which can be obtained by ring opening, for example polyamides of the polycaprolactam type, and also polymers which are obtainable either by polyaddition or by polycondensation, such as polyethers or polyacetals, (c) Polycondensation products or polycondensates based on bifunctional or polyfunctional compounds with condensable groups, their homocondensation and co-condensation products and also aftertreatment products, for example polyesters, especially saturated polyesters (for example polyesters of ethylene glycol terephthalic acid) or unsaturated polyesters (for example maleic acid/dialcohol polycondensates and their crosslinking products with copolymerisable vinyl monomers), unbranched and branched polyesters (also including those based on polyhydric alcohols, for example alkyd resins), polyesters, polyamides (for example hexamethylenediamine adipate), maleate resins, melamine resins, their precondensates and analogues, polycarbonates and silicones, (d) Polyaddition products, such as polyurethanes (crosslinked and uncrosslinked) and epoxide resins.

II. Regenerated man-made organic materials, for example cellulose esters of varying degrees of esterification (so-called 2½-acetate or triacetate) or cellulose ethers, regenerated cellulose (viscose or cuprammonium cellulose), or their aftertreatment products, and casein plastics.

III. Natural organic materials of animal or vegetable origin, for example based on cellulose or proteins, such as cotton, wood, linen, silk, natural varnish gums, starch and casein.

The organic materials to be optically brightened can be in the most diverse states of processing (raw materials, semi-finished goods or finished goods). On the other hand, they can be in the form of structures of the most diverse shapes, for example predominantly three-dimensionally expanded structures, such as sheets, profiles, injection mouldings, various machined articles, chips, granules or foams, and also predominantly two-dimensional structures, such as films, foils, lacquers, coverings, impregnations and coatings, or predominantly one-dimensional bodies, such as filaments, fibres, flocks and wires. The said materials can, on the other hand, also be in an unshaped state, in the most diverse homogeneous or inhomogeneous forms of division, as for example in the form of powders, solutions, emulsions, dispersions, latices, pastes or waxes.

Fibrous materials can be, for example, in the form of endless filaments (stretched or unstretched), staple fibres, flocks, hanks, textile filaments, yarns, threads, non-wovens, felts, waddings, flocked structures or woven textile or bonded textile fabrics, knitted fabrics and papers, cardboards or paper pulps.

The compounds to be used according to the invention are of importance, inter alia, for the treatment of organic textile materials, especially woven textile fabrics. If fibres, which can be in the form of staple fibres or endless filaments or in the form of hanks, woven fabrics, knitted fabrics, fleeces, flocked substrates or bonded fabrics, are to be optically brightened according to the invention, this is advantageously effected in an aqueous medium, in which the compounds in question are present in a finely divided form (suspensions, so-called microdispersions or optionally solutions). If desired, dispersing agents, stabilisers, wetting agents and further assistants can be added during the treatment.

Depending on the type of brightener compound used, it can be advantageous to carry out the treatment in a neutral or alkaline or acid bath. The treatment is usually carried out at temperatures between 20° and 140° C., for example at the boiling point of the bath or near it (about 90° C.). Solutions or emulsions in organic solvents can also be used for the finishing according to the invention of textile substrates, as is practised in the dyeing industry in so-called solvent dyeing (pad-thermofixation, or exhaust dyeing processes in dyeing machines).

The novel fluorescent brightening agents of the present invention can also be added to, or incorporated in, the materials before or during their shaping. Thus, for example, they can be added to the compression moulding composition or injection moulding composition during the manufacture of films, sheets (for example incorporated in polyvinyl chloride in a roll mill at elevated temperature) or mouldings.

If the fashioning of man-made synthetic or regenerated man-made organic materials is effected by spinning processes or from spinning solutions/melts, the fluorescent brightening agents can be applied by the following processes:

addition to the starting substances (for example monomers) or intermediates (for example precondensates or prepolymers), i.e. before or during the polymerisation, polycondensation or polyaddition, sprinkling in powder form on polymer chips or granules for spinning solutions/melts, bath dyeing of polymer chips or granules for spinning solutions/melts, metered addition to spinning melts or spinning solutions, and application to the spun tow before stretching.

The novel fluorescent brightening agents of the present invention can, for example, also be employed in the following use forms:

(a) in mixtures with dyes (shading) or pigments (coloured pigments or especially, for example, white pigments), or as an additive to dye baths, printing pastes, discharge pastes or reserve pastes, or for the aftertreatment of dyeings, prints or discharge prints.

(b) in mixtures with carriers, wetting agents, plasticisers, swelling agents, antioxidants, light stabilisers, heat stabilisers and chemical bleaching agents (chlorite bleach or bleaching bath additives), (c) in mixtures with crosslinking agents or finishing agents (for example starch or synthetic finishes), and in combination with a wide variety of textile finishing processes, especially synthetic resin finishes (for example creaseproof finishes such as "wash-and-wear", "permanent-press" or "no-iron"), as well as flameproof finishes, soft-handle finishes, anti-soiling finishes or antistatic finishes, or antimicrobial finishes, (d) incorporation of the fluorescent brightening agents into polymeric carrier materials (polymerisation, polycondensation or polyaddition products), in dissolved or dispersed form, for use, for example, in coating agents, impregnating agents or binders (solutions, dispersions and emulsions) for textiles, non-wovens, paper and leather, (e) as additives to master batches, (f) as additives to a wide variety of industrial products in order to render these more marketable (for example improving the appearance of soaps, detergents and pigments), (g) in combination with other fluorescent brightening substances, (h) in spinning bath preparations, i.e. as additives to spinning baths which are used for improving the slip for the further processing of synthetic fibres, or from a special bath before the stretching of the fibre, (i) as scintillators for various purposes of a photographic nature, for example for electrophotographic reproduction or supersensitising, and (j) depending on the substitution, as laser dyes.

If the brightening process is combined with textile treatment or finishing methods, the combined treatment can in many cases advantageously be carried out with the aid of appropriate stable preparations which contain the fluorescent brightener compounds in such a concentration that the desired white effect is achieved.

In certain cases, the fluorescent brighteners are made fully effective by an aftertreatment. This can be, for example, a chemical treatment (for example acid treatment), a thermal treatment (for example heat) or a combined chemical/thermal treatment. Thus, for example, the appropriate procedure to follow in the fluorescent brightening of a number of fibre substrates, for example polyester fibres, with the fluorescent brightening agents of the present invention is to impregnate these fibres with the aqueous dispersions (or optionally also solution) of the brighteners at temperatures below 75° C., for example at room temperature, and to subject them to a dry heat treatment at temperatures above 100° C., it being generally advisable additionally to dry the fibrous material beforehand at a moderately elevated temperature, for example at not less than 60° C. to about 130° C. The heat treatment in the dry state is then advantageously carried out at temperatures between 120° and 125° C., for example by heating in a drying chamber, by ioning within the specified temperature range or by treatment with dry, superheated steam. The drying and dry heat treatment can also be carried out in immediate succession or combined in a single operation.

The amount of the novel fluorescent brightening agents to be used according to the invention, based on the material to be optically brightened, can vary within wide limits. A marked and lasting effect can be achieved even with very small amounts, for example amounts of 0.0001 percent by weight in certain cases. However, it is also possible to use amounts of up to about 0.8 percent by weight and, in some cases, up to about 2 percent by weight. For most practical purposes, it is preferable to use amounts of between 0.0005 and 0.5 percent by weight.

For various reasons it is often advantageous not to use the fluorescent brighteners by themselves, i.e. pure, but in admixture with a wide variety of assistants and extenders, for example anhydrous sodium sulphate, sodium sulphate decahydrate, sodium chloride, sodium carbonate, alkali metal phosphates, such as sodium or potassium orthophosphate, sodium or potassium pyrophosphate and sodium or potassium tripolyphosphates, or alkali metal silicates.

In the examples, parts and percentages are always by weight, unless otherwise stated. Unless indicated to the contrary, melting points and boiling points are uncorrected.

EXAMPLE 1

14.9 g of 2-(p-diethylphosphonomethyl-phenyl)-5,7-dimethylbenzoxazole are dissolved, with stirring, in 60 ml of anhydrous dimethylformamide at room temperature, the air being displaced by nitrogen. 2.4 g of sodium methylate (purity: 92.8%) are then introduced in the course of 5 minutes and subsequently a solution of 8 g of 2-(p-formylphenyl)-4-cyano-2H-1,2,3-triazole, dissolved in 100 ml of anhydrous dimethylformamide, is added dropwise in the course of 20 minutes, the temperature rising to 40° C. The reaction mixture is stirred at 40° to 45° C. for a further 4 hours and then discharged into 300 ml of methanol and the product which has crystallised out is filtered off with suction, washed well with methanol and dried in vacuo at 50° to 60° C. After twice recrystallising from chlorobenzene with the aid of bleaching earth, 8.1 g of the compound of the formula

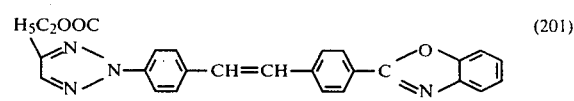

(101)

are obtained in the form of a light yellow crystal powder.

Melting point: not sharp, between 285° and 320° C.

EXAMPLE 2

6.9 g of 2-(p-diethylphosphonomethyl-phenyl)-benzoxazole and 4.9 g of 2-(p-formyl-phenyl)-4-carboethoxy-2H-1,2,3-triazole are dissolved, with stirring, in 40 ml of anhydrous dimethylformamide at 40° C., the air being displaced by nitrogen. 1.4 g of sodium methylate (purity: 92.8%) are introduced in portions in the course of 15 minutes. The reaction mixture is then stirred at 40° to 45° C. for a further 4 hours, discharged into 100 ml of methanol and neutralised with formic acid and the product is filtered off with suction, washed with methanol and dried in vacuo. After recrystallisation from chlorobenzene with the aid of bleaching earth, 3.9 g of the compound of the formula

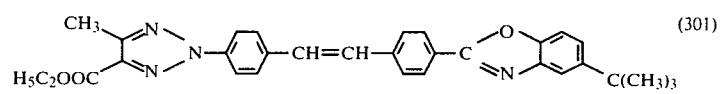

(201)

are obtained in the form of a light yellow crystal powder.

Melting point: not sharp, at 296° to 298° C.

EXAMPLE 3

11.9 g of 2-(p-diethylphosphonomethyl-phenyl)-4-methyl-5-carboethoxy-2H-1,2,3-triazole (purity: 80%) and 7.7 g of 2-(p-formyl-phenyl)-5-t-butyl-benzoxazole are dissolved, with stirring, in 150 ml of anhydrous dimethylformamide at 40° C., the air being displaced by nitrogen. 1.6 g of sodium methylate (purity: 92.8%) are introduced in portions in the course of 15 minutes. The reaction mixture is stirred at 40° to 45°C. for a further 5 hours, discharged into 150 ml of methanol and neutralised with formic acid and the product is filtered off with suction, washed with methanol and dried in vacuo. After recrystallisation from toluene with the aid of bleaching earth, 3.1 g of the compound of the formula

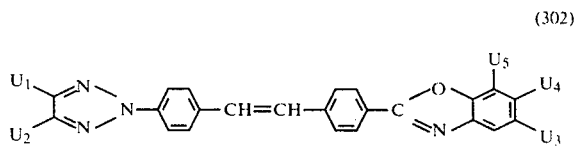

(301)

are obtained in the form of a luminous light yellow crystal powder.

Melting point: 231° to 232° C.

The compounds of the formula (302)

listed in Table I which follows are prepared in an analogous manner.

TABLE I

| Compound No. | $U_1$ | $U_2$ | $U_3$ | $U_4$ | $U_5$ | Melting point: °C. |
|---|---|---|---|---|---|---|
| 303 | —H | —CN | —H | —H | —H | 311–314* |

TABLE I-continued

| Compound No. | U₁ | U₂ | U₃ | U₄ | U₅ | Melting point: °C. |
|---|---|---|---|---|---|---|
| 304 | —H | —CN | —CH₃ | —H | —H | 278* |
| 305 | —H | —CN | —C(CH₃)₃ | —H | —H | 284–285* |
| 306 | —H | —COOCH₃ | —CH₃ | —H | —CH₃ | 202–205* |
| 307 | —H | —COOCH₃ | —C(CH₃)₃ | —H | —H | 257–259 |
| 308 | —H | —COOC₂H₅ | —CH₃ | —H | —CH₃ | 204–206* |
| 309 | —H | —COOCH(CH₃)₂ | —H | —H | —H | 289–292* |
| 310 | —H | —COOCH(CH₃)₂ | —CH₃ | —H | —CH₃ | 190–192* |
| 311 | —CH₃ | —COOCH₃ | —H | —H | —H | 227–229* |
| 312 | —CH₃ | —COOCH₃ | —C(CH₃)₃ | —H | —H | 229–230 |
| 313 | —CH₃ | —COOCH₃ | —H | —OCH₃ | —H | 190–200* |
| 314 | —CH₃ | —COOCH₃ | —OCH₃ | —H | —H | 195* |
| 315 | —CH₃ | —COOCH₃ | —CH₃ | —H | —CH₃ | 203–205 |
| 316 | —CH₃ | —COOC₂H₅ | —H | —H | —H | 254–256* |
| 317 | —CH₃ | —COOC₂H₅ | —H | —O—C₆H₅ | —H | 208–210 |
| 318 | —CH₃ | —COOC₂H₅ | —CH₃ | —H | —H | 192–193 |
| 319 | —CH₃ | —COOC₂H₅ | —CH₃ | —H | —CH₃ | 210–212 |
| 320 | —CH₃ | —COOC₂H₅ | —H | —OCH₃ | —H | 280–282 |
| 321 | —CH₃ | —COOC₂H₅ | —OCH₃ | —H | —H | 226–229* |
| 322 | —CH₃ | —COOC₂H₅ |  | —H | —H | 298–300* |
| 323 | —CH₃ | —COOC₂H₅ | —CH₃ | —CH₃ | —H | 245–285* |
| 324 | —CH₃ | —COOCH(CH₃)₂ | —H | —H | —H | 225* |
| 325 | —CH₃ | —COOCH(CH₃)₂ | —C(CH₃)₃ | —H | —H | 249–251 |
| 326 | —CH₃ | —COOCH(CH₃)₂ | —H | —OCH₃ | —H | 214–216* |
| 327 | —CH₃ | —COOCH(CH₃)₂ | —OCH₃ | —H | —H | 218–220* |
| 328 | —CH₃ | —COOCH(CH₃)₂ | —CH₃ | —H | —CH₃ | 190–192 |
| 329 |  | —COOCH₃ | —H | —H | —H | 227–230 |
| 330 |  | —COOCH₃ | —OCH₃ | —H | —H | 228–230* |
| 331 |  | —COOCH₃ | —C(CH₃)₃ | —H | —H | 233–234 |
| 332 |  | —COOCH₃ | —CH₃ | —H | —CH₃ | 203–204 |
| 333 |  | —COOC₂H₅ | —CH₃ | —H | —CH₃ | 192–198* |
| 334 |  | —COOC₂H₅ | —H | —H | —H | 217–228* |
| 335 |  | —COOC₂H₅ | —OCH₃ | —H | —H | 242–247 |
| 336 |  | —COOCH(CH₃)₂ | —OCH₃ | —H | —H | 233–235 |
| 337 |  | —COOCH(CH₃)₂ | —CH₃ | —H | —CH₃ | 171–173 |
| 338 |  | —COOCH(CH₃)₂ | —H | —H | —H | 222–224 |
| 339 |  | —COO(CH₂)₂CH₃ | —C(CH₃)₃ | —H | —H | 227–229 |
| 340 |  | —COO(CH₂)₂CH₃ | —CH₃ | —H | —CH₃ | 183–185* |
| 341 |  | —COO(CH₂)₂CH₃ | —H | —H | —H | 219–221 |
| 342 | —CH₃ | —CN | —H | —H | —H | 319–324 |
| 343 | —CH₃ | —CN | —H | —OCH₃ | —H | 324–327 |
| 344 | —CH₃ | —CN | —C(CH₃)₃ | —H | —H | 278–279 |
| 345 | —CH₃ | —CN | —CH₃ | —H | —CH₃ | 265–267 |
| 346 | —CH₃ | —CN | —OCH₃ | —H | —H | 328–331* |
| 347 |  | —CN | —H | —H | —H | 294–296* |
| 348 |  | —CN | —OCH₃ | —H | —H | 266–269* |

TABLE I-continued

| Compound No. | U₁ | U₂ | U₃ | U₄ | U₅ | Melting point: °C. |
|---|---|---|---|---|---|---|
| 349 | phenyl | —CN | —CH₃ | —H | —CH₃ | 285–286 |
| 350 | phenyl | —CN | —C(CH₃)₃ | —H | —H | 247–249 |
| 351 | phenyl | —CN | —CH₃ | —H | —H | 270–271 |
| 352 | phenyl | —CN | —H | —CH₃ | —H | 272–274 |
| 353 | CH₃— | —COOC₂H₅ | —H | —CH₃ | —H | 280* |
| 354 | CH₃— | —COOC₂H₅ | —H | —H | —CH₃ | 211–213 |
| 355 | phenyl | —COO(CH₂)₂CH₃ | —H | —H | —CH₃ | 182–184 |
| 356 | phenyl | —COOCH(CH₃)₂ | —H | —H | —CH₃ | 185–187 |
| 357 | phenyl | —COOC₂H₅ | —C(CH₃)₃ | —H | —H | 240–241 |
| 358 | phenyl | —COOCH(CH₃)₂ | —C(CH₃)₃ | —H | —H | 167–169 |
| 359 | phenyl | —COO(CH₂)₂CH₃ | —OCH₃ | —H | —H | 227–230 |

*not sharp; does not give a clear melt.

EXAMPLE 4

In a manner analogous to that described in Examples 1 and 2, the compounds of the formulae

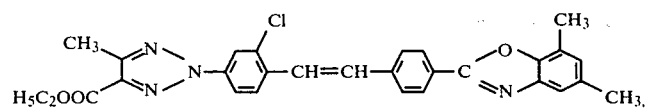

melting point: 218 to 219° C.,

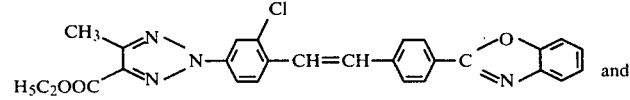

melting point: 236 to 238° C.

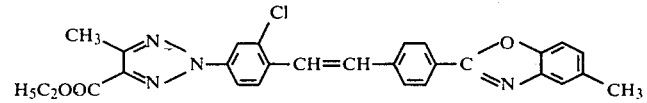

melting point: 223 to 224° C.

are obtained using the aldehyde of the formula

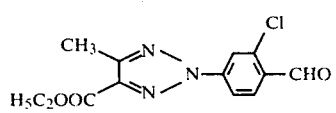

and the phosphonates of the formulae

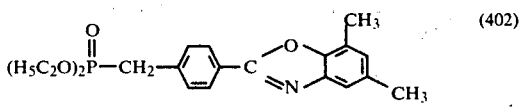 (402)

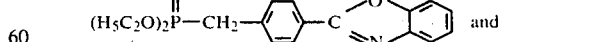 (403)

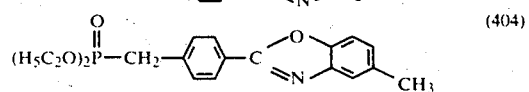 (404)

respectively.

EXAMPLE 5

12 g of the compound of the formula (319) are dissolved in 600 ml of 2-methoxy-ethanol at 120° C. After cooling to 95° C., 5 g of 30% strength sodium hydroxide solution are added dropwise in the course of 10 minutes, the mixture is stirred for a further 2 hours at 95° to 100° C. and cooled and the product which has crystallised out is filtered off with suction and dried in vacuo. This gives 8.1 g of the compound of the formula

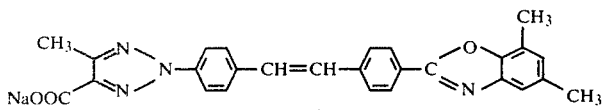 (501)

melting point: >300° C.

8 g of this compound are suspended in 110 ml of chlorobenzene and 0.5 ml of dimethylformamide. 10 ml of thionyl chloride are added dropwise at 22° C. in the course of 10 minutes, the temperature rising to 33° C. The suspension is then heated to 95° C. and stirred for 1½ hours. After cooling, the product which has crystallised out is filtered off with suction, washed with hexane and dried in vacuo. After recrystallisation from chlorobenzene, 6.2 g of the acid chloride of the formula

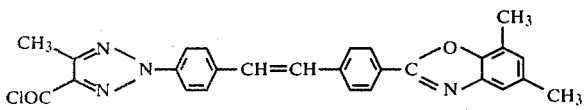 (502)

are obtained.

Melting point: 244° to 247° C.

6.1 g of this acid chloride are suspended in 100 ml of toluene. 10 ml of diethylamine are added dropwise at 45° C. in the course of 10 minutes, the mixture is then stirred for 2 hours at 40° to 45° C. and cooled, and the product which has crystallised out is filtered off with suction. After repeated recrystallisation from toluene, 0.8 g of the compound of the formula

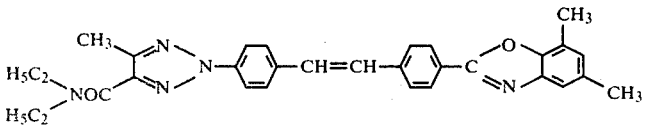 (503)

is obtained.

Melting point: 181° to 183° C.

Preparation of the Starting Materials Used

A. 2-(p-Formyl-phenyl)-4-cyano-2H-1,2,3-triazole 374 g of the p-tolylhydrazone of diisonitrosoacetone of the formula

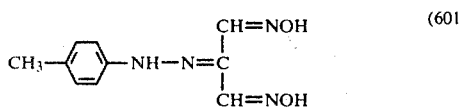 (601)

are introduced in portions in the course of 30 minutes into 1,400 ml of acetic anhydride heated to 60° C., the temperature of the reaction mixture rising to 70° C. The reaction mixture is then refluxed for a further 6 hours. After evaporating to dryness in vacuo, the dark residue is distilled under a high vacuum (boiling point: 111° to 124° C. at 0.2 mm Hg). After recrystallising the distillate from 2 liters of methanol with the aid of active charcoal, 174 g of 2-(p-tolyl)-4-cyano-2H-1,2,3-triazole with a melting point of 107° to 108° C. are obtained.

46.1 g of 2-(p-tolyl)-4-cyano-2H-1,2,3-triazole are dissolved in 1,000 ml of carbon tetrachloride at 75° C., with stirring. 44.5 g of N-bromosuccinimide and 2.5 g of α,α'-azo-bis-isobutyronitrile are then uniformly introduced in portions in the course of 30 minutes. The reaction mixture is then refluxed for a further 5 hours, the succinimide which has crystallised out is filtered off from the hot mixture, the filtrate is cooled to 0° C. and the product which has crystallised out is filtered off with suction, stirred with 500 ml of water, filtered off with suction, washed well with about 3 liters of water and dried in vacuo at 40° to 50° C. This gives 39.6 g of 2-(p-bromomethyl-phenyl)-4-cyano-2H-1,2,3-triazole with a melting point of 147° to 148° C.

4.6 g of sodium are dissolved in 300 ml of absolute ethanol, with stirring and whilst passing a vigorous stream of nitrogen over the mixture. 23.2 g of 2-nitropropane (purity: about 95%) are then added dropwise at 21° C. in the course of 5 minutes and the reaction mixture is stirred at 20° to 25° C. for a further 2 hours. 52.6 g of 2-(p-bromomethyl-phenyl)-4-cyano-2H-1,2,3-triazole are then introduced and the reaction mixture is slowly heated up to the reflux temperature and refluxed for 2 hours. After cooling, the product which has crystallised out is filtered off with suction, stirred with 500 ml of water, again filtered off with suction and washed well with about 2 liters of water. This gives 21.8 g of 2-(p-formyl-phenyl)-4-cyano-2H-1,2,3-triazole with a melting point of 148° to 150° C.

B. 2-(p-Formyl-phenyl)-4-carboethoxy-2H-1,2,3-triazole 73.7 g of 2-(p-tolyl)-4-cyano-2H-1,2,3-triazole in a mixture of 240 ml of glacial acetic acid and 320 ml of hydrobromic acid (48% strength) are refluxed for 23 hours, the reaction mixture is cooled to 0° to 5° C. and the product which has crystallised out is filtered off with suction, washed with water until neutral and dried in vacuo at 70° to 80° C. This gives 78.9 g of 2-(p-tolyl)-4-carboxy-2H-1,2,3-triazole with a melting point of 209° to 211° C.

77.2 g of 2-(p-tolyl)-4-carboxy-2H-1,2,3-triazole are suspended in 160 ml of chlorobenzene, 160 ml of thionyl chloride are added and the reaction mixture is heated to 80° C. in the course of 2 hours and stirred at 80° to 85° C. for about 8 hours. After cooling to room temperature, the reaction mixture is evaporated to dryness in vacuo and the crystalline residue is recrystallised from 200 ml of benzine. After drying in vacuo, this gives 75.4 g of the corresponding carboxylic acid chloride with a melting point of 87° to 89° C.

59 g of the carboxylic acid chloride of 2-(p-tolyl)-4-carboxy-2H-1,2,3-triazole are introduced at room temperature into 800 ml of absolute ethanol. On slowly heating up to the reflux temperature, the product goes into solution. The solution is refluxed for a further 3 hours, 600 ml of ethanol are distilled off, the reaction mixture is cooled to 0° to 5° C. and the product which has crystallised out is filtered off with suction and dried in vacuo. This gives 55.2 g of 2-(p-tolyl)-4-carboethoxy-2H-1,2,3-triazole with a melting point of 61° to 62° C.

55.1 g of 2-(p-tolyl)-4-carboethoxy-2H-1,2,3-triazole are dissolved in 1,000 ml of carbon tetrachloride at 75° C., with stirring. 42.4 g of N-bromosuccinimide and 2.5 g of α,α-azoisobutyronitrile are then introduced in portions in the course of 2 hours and the reaction mixture is then refluxed for a further 5 hours. The succinimide which has crystallised out is then filtered off from the hot mixture, the filtrate is cooled to 0° to 5° C. and the product which has crystallised out is filtered off with suction, stirred with water, again filtered off with suction and washed well with water. After drying in vacuo, this gives 46.6 g of 2-(p-bromomethylphenyl)-4-carboethoxy-2H-1,2,3-triazole with a melting point of 148° to 149° C.

3.5 g of sodium are dissolved in 250 ml of absolute ethanol, with stirring and whilst passing a vigorous stream of nitrogen over the mixture. 18 g of 2-nitropropane are then added dropwise at 15° C. in the course of 15 minutes, the mixture is stirred for a further 1 hour at room temperature, 46.5 g of 2-(p-bromomethyl-phenyl)-4-carboethoxy-2H-1,2,3-triazole are introduced in the course of 15 minutes, 250 ml of dimethylformamide are added, the reaction mixture is stirred for a further 20 hours at room temperature and poured into 2,000 ml of water and the product which has crystallised out is filtered off with suction and washed well with water. After drying in vacuo, this gives 35.8 g of 2-(p-formyl-phenyl)-4-carboethoxy-2H-1,2,3-triazole with a melting point of 126° to 129° C.

If methanol or isopropanol is used in place of ethanol in the reaction with the carboxylic acid chloride of 2-(p-tolyl)-4-carboxy-2H-1,2,3-triazole, the corresponding methyl ester or, respectively, isopropyl ester is obtained. These esters can be converted, in the manner described above, into 2-(p-formyl-phenyl)-4-carbomethoxy-2H-1,2,3-triazole (melting point: 125° to 127° C.) and, respectively, 2-(p-formyl-phenyl)-4-carboisopropoxy-2H-1,2,3-triazole (melting point: 100° to 102° C.).

C.
2-(p-Formyl-phenyl)-4-methyl-5-carboethoxy-2H-1,2,3-triazole 597 g of a water-moist suction filter cake, containing 323 g of ethyl β-oxo-α-p-tolylhydrazono-butyrate, 486 g of copper-II chloride dihydrate and 1,000 g of ammonium acetate are refluxed in 6.8 liters of absolute alcohol for 2 hours, with stirring. The reaction mixture is then poured onto 8 kg of ice and 500 ml of concentrated hydrochloric acid and the product which has crystallised out is filtered off with suction and washed well with water. The moist suction filter cake is dissolved in 3 liters of hexane, the water is separated off and the solution is dried with anhydrous sodium sulphate and, after separating off the sodium sulphate, evaporated to dryness. This gives 298.5 g of 2-(p-tolyl)-4-methyl-5-carboethoxy-2H-1,2,3-triazole with a melting point of 47° to 48° C.

122.6 g of 2-(p-tolyl)-4-methyl-5-carboethoxy-2H-1,2,3-triazole are dissolved in 2,000 ml of carbon tetrachloride at 75° C., with stirring. 89 g of N-bromosuccinimide and 5 g of α,α'-azo-bis-isobutyronitrile are then introduced in the course of 6 hours, with continuous refluxing of the mixture, and the reaction mixture is refluxed for a further 1 hour. The reaction mixture is filtered hot, with suction, the filtrate is evaporated to dryness and the crystalline residue is stirred with water, filtered off with suction, washed well with water and dried in vacuo at 40° to 50° C. This gives 157.6 g of 2-(p-bromomethyl-phenyl)-4-methyl-5-carbomethoxy-2H-1,2,3-triazole with a melting point of 122° to 125° C.

4.6 g of sodium are dissolved in 330 ml of absolute alcohol, with stirring and whilst passing a vigorous stream of nitrogen over the mixture. After cooling to 18° C., 23.2 g of 2-nitropropane are added dropwise in the course of 15 minutes and the reaction mixture is stirred for a further one hour at room temperature. 64.8 g of 2-(p-bromomethylphenyl)-4-methyl-5-carboethoxy-2H-1,2,3-triazole are then introduced, 330 ml of dimethylformamide are added and the reaction mixture is stirred for 22 hours at room temperature. The reaction mixture is then discharged into 2 liters of water and the product which has crystallised out is filtered off with suction, dried in vacuo at 50° to 60° C. and recrystallised from 1 liter of hexane with the aid of bleaching earth. This gives 25.8 g of 2-(p-formyl-phenyl)-4-methyl-5-carboethoxy-2H-1,2,3-triazole with a melting point of 97° to 99° C.

D.
2-(p-Formyl-phenyl)-4-methyl-5-carboisopropoxy-2H-1,2,3-triazole and
2-(p-formyl-phenyl)-4-methyl-5-carbomethoxy-2H-1,2,3-triazole 412 g of 2-(p-tolyl)-4-methyl-5-carboethoxy-2H-1,2,3-triazole are dissolved in 4,000 ml of 2-methoxyethanol at 98° C., with stirring. 336 g of 30% strength sodium hydroxide solution are then added slowly dropwise and the mixture is then refluxed for one hour. After cooling to 95° C., 1,000 ml of water are added, the resulting solution is filtered to give a clear filtrate, the filtrate is rendered strongly acid by adding 300 ml of concentrated hydrochloric acid and cooled and the product which has precipitated is filtered off with suction, washed with 20 liters of water until neutral and dried at 120° C. in vacuo. This gives 328.8 g of 2-(p-tolyl)-4-methyl-5-carboxy-2H-1,2,3-triazole with a melting point of 230° to 232° C.

Conversion into the corresponding carboxylic acid chloride and reaction with isopropanol or methanol, analogously to the procedure described in Preparation Instructions B, gives 2-(p-tolyl)-4-methyl-5-carboisopropoxy-2H-1,2,3-triazole (melting point: 54° to 55° C.) and, respectively, 2-(p-tolyl)-4-methyl-5-carbomethoxy-2H-1,2,3-triazole (melting point: 101° to 102° C.). Bromination with N-bromosuccinimide and reaction with 2-nitropropane, analogously to the procedure described in Preparation Instructions C, gives 2-(p-formyl-phenyl)-4-methyl-5-carboisopropoxy-2H-1,2,3-triazole (melting point: 92° to 95° C.) and, respectively, 2-(p-formyl-phenyl)-4-methyl-5-carbomethoxy-2H-1,2,3-triazole (melting point: 94° to 96° C.).

E.
2-(p-Diethylphosphonomethyl-phenyl)-4-methyl-5-carboethoxy-2H-1,2,3-triazole 155.6 g of 2-(p-bromomethyl-phenyl)-4-methyl-5-carboethoxy-2H-1,2,3-triazole in 430 ml of triethyl phosphite are heated to 150° C. in the course of 2½ hours and the mixture is kept at this temperature for 3 hours, with stirring, ethyl bromide distilling off. The reaction mixture is evaporated under a waterpump vacuum. The residual dark viscous oil is dissolved in 300 ml of methylene chloride and, after the addition of bleaching earth, the solution is filtered to give a clear filtrate and 300 ml of hexane are added to the filtrate. The resulting mixture is then concentrated to 200 ml and cooled to 0° to 5° C. and the product which has crystallised out is filtered off with suction and dried in vacuo. This gives 56.6 g of 2-(p-diethylphosphonomethyl-phenyl)-4-methyl-5-carboethoxy-2H-1,2,3-triazole of the formula

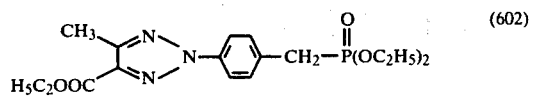

(602)

Melting point: 60° to 62° C.

F.
2-(p-Formyl-phenyl)-4-methyl-5-cyano-2H-1,2,3-triazole 104 g of the carboxylic acid chloride of 2-(p-tolyl)-4-methyl-5-carboxy-2H-1,2,3-triazole are dissolved in 2,000 ml of toluene at 65° to 70° C. Ammonia gas is passed in for 3 hours, with good stirring. After cooling, the product which has crystallised out is filtered off with suction, washed well with water and dried in vacuo. This gives 86.5 g of the compound of the formula

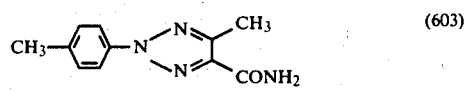

(603)

Melting point: 183° to 184° C.

64.8 g of this compound are dissolved in 600 ml of chlorobenzene at 105° C., with stirring. 14.1 ml of phosphorus oxychloride are then added dropwise in the course of 30 minutes, at 105° to 110° C., and the reaction mixture is stirred at this temperature for a further 18 hours. After filtering to give a clear filtrate, the chlorobenzene is removed by steam distillation. After cooling, the product is taken up in 900 ml of chloroform, the solution is dried with anhydrous sodium sulphate, the chloroform is completely distilled off in a rotary evaporator and the residue is dried in vacuo at 60° C. This gives 54 g of 2-(p-tolyl)-4-methyl-5-cyano-2H-1,2,3-triazole with a melting point of 105° to 106° C. Bromination with N-bromosuccinimide and reaction with 2-nitropropane, analogously to the procedure described in Preparation Instructions C, gives 2-(p-formyl-phenyl)-4-methyl-5-cyano-2H-1,2,3-triazole of the formula

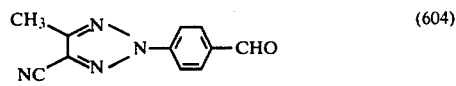

(604)

Melting point: 137° to 139° C.

G.
2-(p-Formyl-phenyl)-4-phenyl-5-carboethoxy-2H-1,2,3-triazole 108.6 g of ethyl β-oxo-α-p-tolylhydrazono-β-phenyl-propionate (obtained by coupling diazotised p-toluidine with ethyl benzoylacetate in alcohol/water), 130.7 g of copper-II chloride dihydrate and 270.2 g of ammonium acetate in 1.8 liters of absolute alcohol are refluxed for 22 hours, with stirring. After cooling, the reaction mixture is poured onto 2 kg of ice and 200 ml of concentrated hydrochloric acid and the product which has precipitated is filtered off with suction, suspended in 500 ml of 2 N hydrochloric acid, again filtered off with suction, washed with a large amount of water until neutral and dried in vacuo. This gives 91.2 g of 2-(p-tolyl)-4-phenyl-5-carboethoxy-2H-1,2,3-triazole with a melting point of 72° to 74° C. After recrystallising twice from alcohol, with the aid of active charcoal, and crystallising once from hexane, with the aid of bleaching earth, the product is obtained as white crystals with a melting point of 74° to 75° C.

Bromination with N-bromosuccinimide and reaction of the resulting bromomethyl compound with 2-nitropropane, analogously to the procedure described in Preparation Instructions C, gives 2-(p-formyl-phenyl)-4-phenyl-5-carboethoxy-2H-1,2,3-triazole of the formula

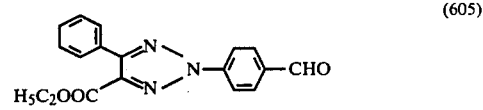

(605)

Melting point: 96° to 97° C.

H.
2-(p-Formyl-phenyl)-4-phenyl-5-carbomethoxy-2H-1,2,3-triazole 261.2 g of 2-(p-tolyl)-4-phenyl-5-carboethoxy-2H-1,2,3-triazole are saponified, analogously to the procedure described in Preparation Instructions D, to the corresponding carboxylic acid of the formula

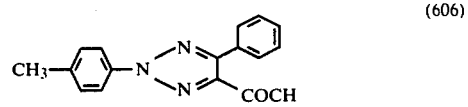

(606)

and the latter is converted into the corresponding carboxylic acid chloride of the formula

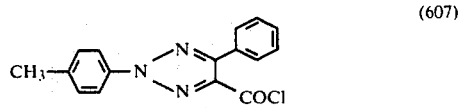

(607)

Reaction with methanol, analogously to the procedure described in Preparation Instructions B, gives the corresponding methyl ester (melting point: 72° to 74° C.), and the aldehyde of the formula

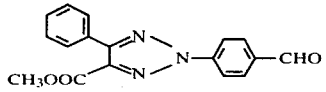
(608)

melting point: 88 to 89° C.

is obtained therefrom by bromination with N-bromosuccinimide and reaction with 2-nitropropane, analogously to the procedure described in Preparation Instructions C.

The aldehydes of the formulae

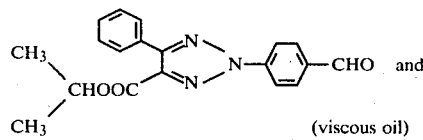
(609)
and (viscous oil)

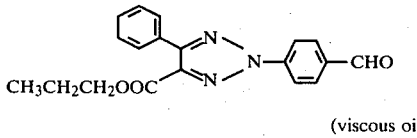
(610)

(viscous oil)

are obtained in an entirely analogous manner.

J. 2-(p-Formyl-phenyl)-4-phenyl-5-cyano-2H-1,2,3-triazole 163.7 g of the acid chloride of the formula

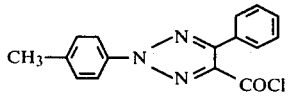
(607)

are dissolved in 2,500 ml of toluene at 60° C., with stirring. A vigorous stream of ammonia gas is passed into the solution for 2 hours at 60° C. to 70° C. After cooling, the product which has crystallised out is filtered off with suction, stirred with water, again filtered off with suction, washed well with water, and dried in vacuo at 60° to 70° C. This gives 145.2 g of the compound of the formula

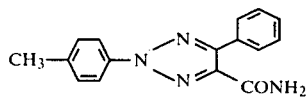
(612)

Melting point: 208° to 209° C.

144.8 g of this product are dissolved in 1,700 ml of chlorobenzene at 115° C., with stirring. 24.5 ml of phosphorus oxychloride are added dropwise in the course of about 10 minutes and the whole is stirred for 23 hours at 110° to 115° C. The slightly turbid solution is filtered to give a clear filtrate, the chlorobenzene is distilled off with steam and, after cooling, the product which has crystallised out is filtered off with suction, washed with water and dried in vacuo at 60° to 70° C. This gives 122 g of the compound of the formula

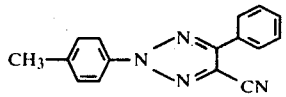
(613)

Melting point: 111° to 115° C. (not sharp).
The aldehyde of the formula

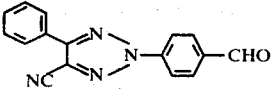

melting point: 127 to 133° C.

is obtained therefrom by bromination with N-bromosuccinimide and reaction with 2-nitropropane, analogously to the procedure described in Preparation Instructions C.

K. 2-(4-Formyl-3-chlorophenyl)-4-methyl-5-carboethoxy-2H-1,2,3-triazole

The aldehyde of the formula

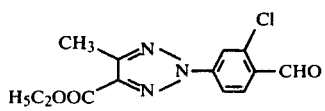
(615)

(melting point: 118 to 119° C.)

is obtained when, analogously to the procedure described in Preparation Instructions C, ethyl β-oxo-α-(3-chloro-4-methylphenyl)-hydrazono-butyrate is converted to the corresponding 2-(3-chloro-4-methylphenyl)-4-methyl-5-carboethoxy-2H-1,2,3-triazole (melting point: 77° to 78° C.), this is reacted with N-bromosuccinimide to give the corresponding bromomethyl compound (melting point: 109° to 111° C.) and this is reacted with 2-nitropropane and sodium ethylate in ethanol/dimethylformamide to give the aldehyde of the formula (615).

The ethyl β-oxo-α-(3-chloro-4-methylphenyl)-hydrazonobutyrate used can be prepared as follows:

566.4 g of 3-chloro-4-methylaniline are dissolved in 1,600 ml of water and 1,000 ml of 36% strength hydrochloric acid and diazotised at 0° to 5° C. with 280 g of sodium nitrite dissolved in 1,200 ml of water. The resulting solution of the diazonium salt is added dropwise in the course of one hour, at 0° to 5° C., to a mixture of 560 g of ethyl acetoacetate, 1,500 ml of ethanol, 2,000 ml of water and 925 g of sodium acetate trihydrate, with stirring, the mixture is stirred for 21 hours at 0° to 5° C. and the product is filtered off with suction, washed well with water and employed as the moist suction filter cake. A sample dried in vacuo at 40° C. has a melting point of 71° to 73° C.

L. 2-(p-Formyl-phenyl)-5-t-butyl-benzoxazole 66.3 g of 2-(p-tolyl)-5-t-butyl-benzoxazole are dissolved in 1,000 ml of carbon tetrachloride at 71° C., with stirring. 49 g of N-bromosuccinimide and 2.5 g of dibenzoyl peroxide are introduced in portions in the course of one hour, at the reflux temperature, whilst irradiating with UV light. A further 7.5 g of dibenzoyl peroxide are then introduced in portions in the course of 5 hours, at the same temperature. The succinimide which has crystallised out is filtered off from the hot reaction mixture and the cooled filtrate is filtered to give a clear solution, the solvent is completely distilled off in vacuo, the residue is stirred with 1,000 ml of water and heated to the boil and the precipitate is filtered off with suction, washed well with water and dried in vacuo at 40° C. After recrystallisation from hexane, the compound of the formula

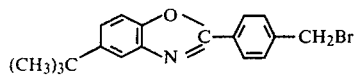 (616)

melting point: 130 to 131° C.

is obtained.

3.7 g of sodium are dissolved in 250 ml of absolute ethanol, with stirring and whilst passing a vigorous stream of nitrogen over the mixture. 19.6 g of 2-nitropropane (purity: about 95%) are then added dropwise in the course of 10 minutes at 20° C. and the mixture is stirred at 20° to 25° C. for about a further one hour. 58.5 g of the compound of the formula (616) and subsequently 250 ml of dimethylformamide are then added, whereupon a slightly exothermic reaction starts and the temperature rises to 35° C. The reaction mixture is stirred for a further 6 hours at room temperature and poured onto 2 kg of ice/water and the product which has crystallised out is filtered off with suction, washed well with water and dried in vacuo. After recrystallisation from 420 ml of benzine, 23.3 g of the compound of the formula

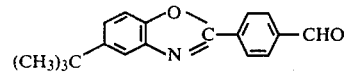 (617)

melting point: 167 to 170° C.

are obtained.

M.

2-(p-Diethylphosphonomethyl)-phenyl)-5-t-butyl-benzoxazole 115.3 g of the compound of the formula (616) in 200 ml of triethyl phosphite are heated to 155° C. in the course of 3 hours, with stirring, and stirred at this temperature for a further 1½ hours, ethyl bromide distilling off through a descending condenser. The excess triethyl phosphite is then distilled off in vacuo and the residue is recrystallised from 750 ml of hexane. This gives 116.8 g of the compound of the formula

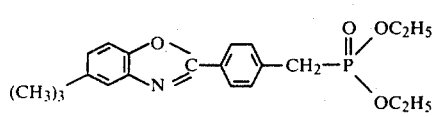 (618)

melting point: 99 to 100° C.

N.

2-(p-Diethylphosphonomethyl-phenyl)-5-phenyl-benzoxazole 92.1 g of 4-phenyl-2-aminophenol are suspended in 600 ml of 2-methoxyethanol at 22° C., with stirring. After adding 46.2 g of sodium bicarbonate, a solution of 104 g of 4-chloromethylbenzoyl chloride in 50 ml of 2-methoxyethanol is added dropwise in the course of 15 minutes, the temperature rising to 38° C. The reaction mixture is stirred at room temperature for a further 4 hours, 700 ml of water and 8 ml of 36% strength hydrochloric acid are added, the product which has crystallised out is filtered off with suction and the product is suspended in 900 ml of ether, again filtered off with suction and washed well with ether. After drying in vacuo, this gives 156.7 g of the compound of the formula

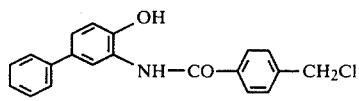 (619)

melting point: 242 to 243° C.

156.4 g of the compound of the formula (619) and 3 g of p-toluenesulphonic acid monohydrate are suspended in 900 ml of dichlorobenzene, with stirring, the air being displaced by nitrogen. The reaction mixture is heated to 170° C. in the course of one hour and a mixture of dichlorobenzene and water distils off through a descending condenser. The mixture is stirred at 170° to 175° C. for a further 4 hours, a further 1 g of p-toluenesulphonic acid monohydrate is added and the mixture is stirred at 170° to 175° C. for a further 3 hours. After this time, 700 ml of dichlorobenzene have distilled off. The mixture is then cooled to 80° C., 1,000 ml of hexane are added, the resulting mixture is cooled and the product which has crystallised out is filtered off with suction, washed with hexane and dried in vacuo. After recrystallising from 1,200 ml of toluene with the aid of bleaching earth, 98.7 g of the compound of the formula

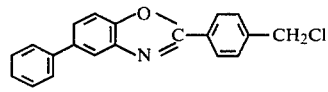 (620)

melting point: 147 to 148° C.

are obtained.

98 g of the compound of the formula (620) in 150 ml of triethyl phosphite are heated to 140° C. in the course of one hour, with stirring, and the mixture is then stirred at 140° to 145° C. for 7 hours, ethyl chloride distilling off. After cooling, the product which has crystallised out is dissolved in chloroform, the solution is filtered to give a clear filtrate, the clear solution is evaporated to dryness, the residue is stirred with hexane and the product is filtered off with suction, washed with hexane and dried in vacuo. This gives 107.7 g of the compound of the formula

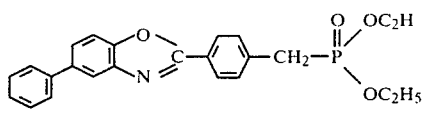
(621)

melting point: 117 to 118° C.

The compounds of the formula

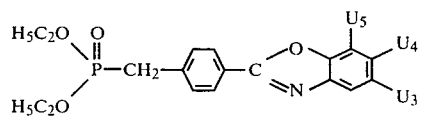
(622)

listed in Table II which follows can be obtained in a manner analogous to that described in Preparation Instructions M and N:

TABLE II

| No. | $U_3$ | $U_4$ | $U_5$ | Preparation Instructions | Melting point: °C. |
|---|---|---|---|---|---|
| 623 | —$CH_3$ | —H | —$CH_3$ | N | 77–79 |
| 624 | —H | —H | —H | M | 87–88 |
| 625 | —$CH_3$ | —H | —H | N | 79–81 |
| 626 | —H | —$OCH_3$ | —H | M | 79–80 |
| 627 | —$OCH_3$ | —H | —H | M | 82–83 |
| 628 | —H | —O—⟨⟩ | —H | M | 99–101 |
| 629 | —$CH_3$ | —$CH_3$ | —H | N | 108–109 |
| 630 | —H | —$CH_3$ | —H | N | 88–89 |
| 631 | —H | —H | —$CH_3$ | N | oil, purity: 72% |

EXAMPLE 6

Polyester fabric (®Dacron 54) is padded at room temperature with an aqueous dispersion which contains, per liter, 1 g of a fluorescent brightening agent of the formula (201) and 1 g of an adduct of about 8 mols of ethylene oxide and 1 mol of p-tert.-octylphenol. The liquid pick-up is 60 to 70%. The fabric is dried at 100° C. and then heated at 220° to 160° C. for 30 seconds to 3 minutes.

The fabric treated in this way shows a strong white effect of good fastness to light.

Similarly good effects are obtained when a fluorescent brightening agent of the formula (305), (306), (308) to (310), (319), (328), (332) to (334), (336), (337), (340), (354) to (356) to (358) is employed in place of the fluorescent brightening agent of the formula (201).

EXAMPLE 7

Modified polyester fabric (®Dacron 64) is padded at room temperature with an aqueous dispersion which contains, per liter, 1 g of a fluorescent brightening agnet of the formula (101) and 1 g of an adduct of about 8 mols of ethylene oxide and 1 mol of p-tert.-octylphenol. The liquid pick-up is 60 to 70%. The fabric is dried at 100° C. and then heated at 220° to 160° C. for 30 seconds to 3 minutes.

The fabric treated in this way shows a strong white effect of good fastness to light.

Similarly good effects are obtained when a fluorescent brightening agent of the formula (201), (301), (303) to (306), (308) to (312), (314) to (319), (321) to (325), (327) to (334), (336) to (341), (345), (350), (353) to (358) or (407) is employed in place of the fluorescent brightening agent of the formula (101).

EXAMPLE 8

1 g of the fluorescent brightening agent of the formula (201) is dispersed in 1,000 ml of water. 100 ml of water which contain 0.06 g of an alkylpolyglycol ether are added to 1.5 ml of this dispersion. Polyester fabric (®Dacron 54) weighing 3 g is added to this fluorescent brightener dispersion, which has been warmed to 60° C. The temperature is raised in the course of 10 to 15 minutes to 95° to 97° C. and this temperature is maintained for 1 hour. The fabric is then rinsed for 2 minutes in running cold water and then dried for 20 minutes at 60° C.

The fabric treated in this way shows a strong white effect.

Similarly good effects are obtained when a fluorescent brightening agent of the formula (306), (309), (310), (314), (316), (318), (327), (328) or (353) is employed in place of the fluorescent brightening agent of the formula (201).

EXAMPLE 9

1 g of the fluorescent brightening agent of the formula (201) is dispersed in 1,000 ml of water. 100 ml of water which contain 0.06 g of an alkylpolyglycol ether are added to 1.5 ml of this dispersion. A modified polyester fabric (®Dacron 64) weighing 3 g is added to this fluorescent brightener dispersion, which has been warmed to 60° C. The temperature is raised to 95° to 97° C. in the course of 10 to 15 minutes and this temperature is maintained for 1 hour. The fabric is then rinsed for 2 minutes in running cold water and then dried for 20 minutes at 60° C.

The fabric treated in this way shows a strong white effect.

Similarly good effects are obtained when a fluorescent brightening agent of the formula (303), (306), (308) to (311), (314) to (316), (318), (319), (321), (327) to (329), (334), (336), (337), (341) or (353) to (355) is employed in place of the fluorescent brightening agent of the formula (201).

EXAMPLE 10

1 g of the fluorescent brightening agent of the formula (306) is dispersed in 1,000 ml of water. 100 ml of water which contain 0.06 g of an alkylpolyglycol ether are added to 3 ml of this dispersion. Polyamide fabric (polyamide 6) weighting 3 g is added to this fluorescent brightener dispersion, which has been warmed to 60° C. The temperature is raised to 95° to 97° C. in the course of 10 to 15 minutes and this temperature is maintained for 30 minutes. The fabric is then rinsed for 2 minutes in running cold water and then dried for 20 minutes at 60° C.

The fabric treated in this way shows a strong white effect of good fastness to light.

Similarly good effects are obtained when a fluorescent brightening agent of the formula (308), (310) or (311) is employed in place of the fluorescent brightening agent of the formula (306).

EXAMPLE 11

1,000 g of polyester granules of the ethylene glycol terephthalate type, containing 0.5% of $TiO_2$ (anatase type) are mixed with 1 g of a compound of the formula (101) in a gyrowheel mixer and the granules treated in this way are spun in an extruder spinning installation at 280° C., to give a multifilament. The resulting filaments show an excellent white effect of good fastness to light.

Similarly good effects are obtained when a fluorescent brightening agent of the formula (303), (305) or (308) is employed in place of the fluorescent brightening agent of the formula (101).

EXAMPLE 12

An intimate mixture of 65 parts of polyvinyl chloride (suspension type), 32 parts of dioctyl phthalate, 3 parts of an epoxidised soya bean oil, 1.5 parts of stabiliser (for example ®Irgastab BC 26), 0.5 part of co-stabiliser (for example ®Irgastab CH 300), 5 parts of TiO₂ (rutile type) and 0.1 part of a compound of the formula (101) is rolled out on a calender at 150° C. to give a film. The resulting film shows a strong white effect of good fastness to light.

Similarly good effects are obtained when a fluorescent brightening agent of the formula (305), (306), (308) or (310) is employed in place of the fluorescent brightening agent of the formula (101).

What is claimed is:

1. A stilbene compound of the formula

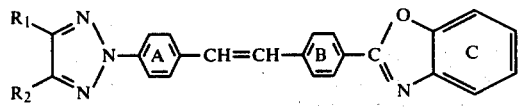

in which the rings A, B and C can carry non-chromophoric substituents, $R_1$ is hydrogen, alkyl which is unsubstituted or substituted by non-chromophoric substituents, or aryl which is unsubstituted or substituted by non-chromophoric substituents, and $R_2$ is a carboxyl group or a functional derivative thereof, a cyano group, a sulphonic acid ester group, a sulphonamide group or a sulphonyl group.

2. A stilbene compound according to claim 1, of the formula

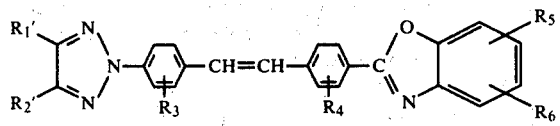

in which $R_1'$ is hydrogen, alkyl having 1 to 8 carbon atoms, alkyl having 1 to 4 carbon atoms which is substituted by halogen, cyano, alkoxy having 1 to 4 carbon atoms or phenyl, it being possible for the phenyl moiety of a phenylalkyl radical also to contain 1 or 2 substituents from the group comprising halogen and alkyl or alkoxy having 1 to 4 carbon atoms, or unsubstituted phenyl or phenyl substituted by 1 or 2 radicals from the group comprising halogen, cyano, alkyl or alkoxy each having 1 to 4 carbon atoms, carboxyl, carbalkoxy, sulphamoyl or alkylsulphonyl, $R_2'$ is cyano, a group of the formula —COOY, in which Y is hydrogen, an alkali metal ion, alkaline earth metal ion, ammonium ion or amine ion or an aliphatic, araliphatic or aromatic radical, a group of the formula —CON(Y₁)(Y₂) or —SO₂N(Y₁)(Y₂), in which Y₁ is hydrogen, an alkyl group having 1 to 8 carbon atoms, a hydroxyalkyl group having 2 to 4 carbon atoms or an unsubstituted phenyl radical or a phenyl radical substituted by chlorine or alkyl or alkoxy each having 1 to 4 carbon atoms and Y₂ is hydrogen, an alkyl group having 1 to 8 carbon atoms or a hydroxyalkyl group having 2 to 4 carbon atoms, or Y₁ and Y₂ together with the nitrogen atom to which they are bonded form a 5-membered to 7-membered non-aromatic heterocyclic ring, which can also contain 1 or 2 further hetero-atoms and can be substituted by alkyl groups having 1 to 4 carbon atoms; or alkylsulphonyl having 1 to 8 carbon atoms or a group of the formula —SO₂—O—Ar or —SO₂—Ar, in which Ar is unsubstituted phenyl or phenyl substituted by 1 or 2 radicals from the group comprising halogen, cyano and alkyl or alkoxy each having 1 to 4 carbon atoms, $R_3$ and $R_4$ independently of one another are hydrogen, chlorine or cyano, $R_5$ is hydrogen, chlorine, cyano or alkyl having 1 to 8 carbon atoms, or together with $R_6$ in the ortho-position is the complement to an alicyclic 5-membered or 6-membered ring, and $R_6$ is hydrogen, chlorine, cyano, alkyl having 1 to 8 carbon atoms, which is unsubstituted or substituted by cyano, carboxyl, carbalkoxy or chlorine, alkoxyalkyl having a total of 2 to 8 carbon atoms, alkoxy having 1 to 8 carbon atoms which is unsubstituted or substituted by cyano, or alkoxyalkoxy having a total of 2 to 8 carbon atoms, alkylsulphonyl having 1 to 8 carbon atoms, a group of the formula —CON(Y₁)(Y₂) or —SO₂N(Y₁)(Y₂), in which Y₁ is hydrogen, an alkyl group having 1 to 8 carbon atoms, a hydroxyalkyl group having 2 to 4 carbon atoms or an unsubstituted phenyl radical or a phenyl radical substituted by chlorine or alkyl or alkoxy each having 1 to 4 carbon atoms, and Y₂ is hydrogen, an alkyl group having 1 to 8 carbon atoms or a hydroxyalkyl group having 2 to 4 carbon atoms, or Y₁ and Y₂ together with the nitrogen atom to which they are bonded form a 5-membered to 7-membered non-aromatic heterocyclic ring, which can also contain 1 or 2 further hetero-atoms and can be substituted by alkyl groups having 1 to 4 carbon atoms; or phenylsulphonyl, phenoxysulphonyl, phenyl, phenoxy or phenylalkyl having 1 to 4 carbon atoms in the alkyl moiety, it being possible for the phenyl radicals of the last-mentioned 5 substituents also to be substituted by one or two radicals from the group comprising chlorine and alkyl and alkoxy each having 1 to 4 carbon atoms, or cyclohexyl or a group of the formula COOY, in which Y is hydrogen, an alkali metal ion, alkaline earth metal ion, ammonium ion or amine ion or an aliphatic, araliphatic or aromatic radical, or $R_6$ together with $R_5$ in the ortho-position is the complement to an alicyclic 5-membered or 6-membered ring.

3. A stilbene compound according to claim 2, of the formula

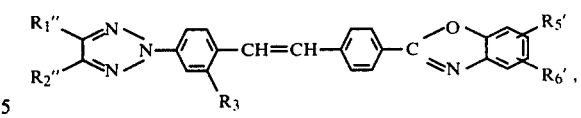

in which $R_1''$ is hydrogen, alkyl having 1 to 4 carbon atoms, benzyl or phenyl, $R_2''$ is cyano, a group of the formula COOY', in which Y' is hydrogen, an alkali metal ion, ammonium ion or amine ion or an alkyl group having 1 to 4 carbon atoms, or a group of the formula —CON(Y₁')(Y₂'), in which Y₁' and Y₂' independently of one another are hydrogen or alkyl having 1 to 4 carbon atoms, or Y₁' and Y₂' together with the nitrogen atom to which they are bonded form a piperidine, dimethylmorpholine or morpholine ring, $R_3$ is hydrogen, chlorine or cyano, $R_5'$ is hydrogen, chlorine or alkyl having 1 to 4 carbon atoms, or together with $R_6'$ in the ortho-position is the trimethylene radical or tetramethylene radical, and R₆' is hydrogen, chlorine, alkyl having 1 to 4 carbon atoms, alkoxy having 1 to 4 carbon atoms, alkylsulphonyl having 1 to 4 carbon atoms, a group of the formula SO₂N(Y₁')(Y₂'), in which Y₁' and Y₂' independently of one another are hydrogen or alkyl having 1 to 4 carbon atoms, or Y₁' and Y₂' together with the nitrogen atom to which they are bonded form a piperidine, dimethylmorpholine or morpholine ring; or phenylsulphonyl, phenoxysulphonyl, phenyl, phenoxy, phenylalkyl having 1 to 4 carbon atoms in the alkyl moiety, cyclohexyl or a group of the formula COOY', in which Y' is hydrogen, an alkali metal ion, ammonium ion or amine ion or an alkyl group having 1 to 4 carbon atoms, or R₆' together with R₅' in the ortho-position is a trimethylene radical or tetramethylene radical.

4. A stilbene compound according to claim 3, of the formula

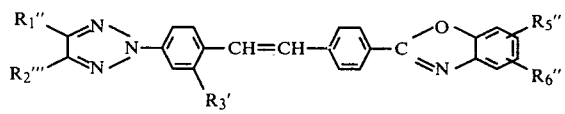

in which R₁" is hydrogen, alkyl having 1 to 4 carbon atoms, benzyl or phenyl, R₂'" is cyano, a carboxyl group or the sodium or potassium salt thereof, carbalkoxy having a total of 2 to 5 carbon atoms or a group of the formula —CON(Y₁")(Y₂"), in which Y₁" and Y₂" independently of one another are hydrogen or alkyl having 1 to 4 carbon atoms, R₃' is hydrogen or chlorine, R₅" is hydrogen, chlorine or alkyl having 1 to 4 carbon atoms and R₆" is hydrogen, alkyl having 1 to 4 carbon atoms, alkoxy having 1 to 4 carbon atoms, phenyl or phenoxy.

5. A stilbene compound according to claim 3, of the formula

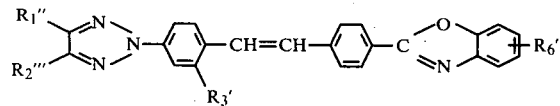

in which R₁", R₂'" and R₃' are as defined in claim 4 and R₆' is hydrogen, chlorine, alkyl having 1 to 4 carbon atoms, alkoxy having 1 to 4 carbon atoms, alkylsulphonyl having 1 to 4 carbon atoms, a group of the formula —SO₂N(Y₁')(Y₂'), in which Y₁' and Y₂' independently of one another are hydrogen or alkyl having 1 to 4 carbon atoms, or Y₁' and Y₂' together with the nitrogen atom to which they are bonded form a piperidine, dimethylmorpholine or morpholine ring; or phenylsulphonyl, phenoxysulphonyl, phenyl, phenoxy, phenylalkyl having 1 to 4 carbon atoms in the alkyl moiety, cyclohexyl or a group of the formula COOY', in which Y' is hydrogen, an alkali metal ion, ammonium ion or amine ion or an alkyl group having 1 to 4 carbon atoms.

6. A stilbene compound according to claim 4, of the formula

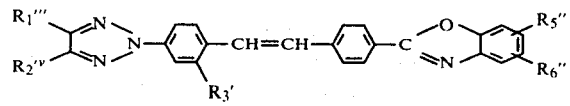

in which R₁'" is hydrogen, methyl or phenyl and R₂" is cyano, carbalkoxy having a total of 2 to 5 carbon atoms or a group of the formula —CON(Y₁")(Y₂"), in which Y₁" and Y₂" independently of one another are hydrogen or alkyl having 1 to 4 carbon atoms, and R₃', R₅" and R₆" are as defined in claim 4.

7. A stilbene compound according to claim 6, of the formula

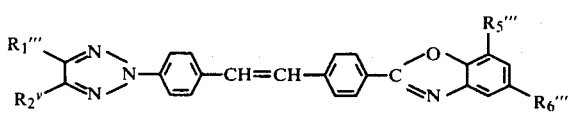

in which R₁'" is hydrogen, methyl or phenyl, R₂ᵛ is carbalkoxy having a total of 2 to 5 carbon atoms, R₅'" is hydrogen or methyl and R₆'" is hydrogen, alkyl having 1 to 4 carbon atoms or methoxy.

8. A process for the fluorescent brightening of high-molecular organic material, which comprises incorporating one or more of the compounds defined in claim 1 into this material or applying one or more of the said compounds to the surface of the material.

9. A process according to claim 8, which comprises applying to, or incorporating in, the material to be whitened 0.001 to 2%, preferably 0.01 to 0.5%, of the respective fluorescent brightening compound, based on the weight of the material to be whitened.

10. A process according to claim 9, which comprises whitening synthetic, high-molecular organic material, preferably made of polyester.

11. A process according to claim 10, which comprises whitening polyester fabric by the pad-bake process.

12. A process according to claim 10, which comprises incorporating the fluorescent brightening compound in a polyester spinning solution/melt and subsequently spinning this spinning solution/melt.

13. High-molecular organic material containing 0.001 to 2, preferably 0.01 to 0.5, percent by weight of one or more of the stilbene compounds defined in claim 1.

* * * * *

UNITED STATES PATENT AND TRADEMARK OFFICE
CERTIFICATE OF CORRECTION

PATENT NO. : 4,261,855
DATED : April 14, 1981
INVENTOR(S) : Kurt Weber

It is certified that error appears in the above—identified patent and that said Letters Patent is hereby corrected as shown below:

Claim 6, Column 32, line 13 reads:

"... in which $R_1'''$ is hydrogen, methyl or phenyl and $R_2''$ is ..."

Should read:

"... in which $R_1'''$ is hydrogen, methyl or phenyl and $R_2^{IV}$ is..."

Signed and Sealed this

Eleventh Day of August 1981

[SEAL]

Attest:

GERALD J. MOSSINGHOFF

Attesting Officer   Commissioner of Patents and Trademarks